(12) United States Patent
Haverkost et al.

(10) Patent No.: US 7,887,573 B2
(45) Date of Patent: Feb. 15, 2011

(54) METHOD AND APPARATUS FOR DEPLOYMENT OF AN ENDOLUMINAL DEVICE

(75) Inventors: Patrick A. Haverkost, Brooklyn Center, MN (US); Paul F. Chouinard, Maple Grove, MN (US); James Weldon, Roslindale, MA (US); Karen McDonald, North Billerica, MA (US); Wade M. Johnson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 168 days.

(21) Appl. No.: 10/081,641

(22) Filed: Feb. 22, 2002

(65) Prior Publication Data

US 2003/0163155 A1 Aug. 28, 2003

(51) Int. Cl.
*A61F 2/06* (2006.01)
*A61M 25/01* (2006.01)
*A61M 25/10* (2006.01)

(52) U.S. Cl. ............. 623/1.11; 623/1.12; 606/198
(58) Field of Classification Search ............ 606/194, 606/108, 198, 200; 623/1.11, 1.12, 2.11; 604/96.01, 99.01, 264, 101.01
See application file for complete search history.

(56) References Cited

U.S. PATENT DOCUMENTS

| | | |
|---|---|---|
| 4,140,126 A | 2/1979 | Choudhury |
| 4,732,152 A | 3/1988 | Wallstén et al. |
| 4,787,899 A | 11/1988 | Lazarus |
| 4,950,227 A | 8/1990 | Savin et al. |
| 5,078,720 A * | 1/1992 | Burton et al. ............... 606/108 |
| 5,122,136 A | 6/1992 | Guglielmi et al. |

(Continued)

FOREIGN PATENT DOCUMENTS

EP 0 637 454 2/1995

(Continued)

OTHER PUBLICATIONS

Notification of Transmittal w/ International Search Report for corresponding international application PCT/US03/04832, dated Aug. 5, 2003.

(Continued)

*Primary Examiner*—Anhtuan T Nguyen
*Assistant Examiner*—Amy Lang
(74) *Attorney, Agent, or Firm*—Brooks, Cameron & Huebsch, PLC (57) ABSTRACT

An introducer deploys an endoluminal device in a distal location from a proximal location. The introducer comprises a retrograde portion, an anterograde portion axially moveable relative to the retrograde portion, a shaft having a distal tip and an anterograde sheath attached to the distal tip, and anchoring means in at least one of the retrograde portion or the anterograde portion for anchoring the device during deployment from its proximal end to its distal end. An inner sheath may be mounted concentrically over the shaft with the endoluminal device mounted concentrically over the inner sheath. The anchoring device may comprise an inflatable balloon mounted radially inside the retrograde portion, a tether, or an extended portion of the endoluminal device confined by a notch in the interface of two sheaths in the retrograde portion of the introducer, or may comprise a holder in the anterograde portion.

15 Claims, 5 Drawing Sheets

U.S. PATENT DOCUMENTS

| | | | |
|---|---|---|---|
| 5,148,548 A | 9/1992 | Meche et al. | |
| 5,158,548 A | 10/1992 | Lau et al. | |
| 5,201,757 A * | 4/1993 | Heyn et al. | 606/198 |
| 5,354,295 A | 10/1994 | Guglielmi et al. | |
| 5,409,495 A * | 4/1995 | Osborn | 623/1.11 |
| 5,415,664 A | 5/1995 | Pinchuk | |
| 5,445,646 A * | 8/1995 | Euteneuer et al. | 606/198 |
| 5,456,694 A | 10/1995 | Marin et al. | |
| 5,480,423 A | 1/1996 | Ravenscroft et al. | |
| 5,591,228 A | 1/1997 | Edoga | |
| 5,609,627 A | 3/1997 | Goicoechea et al. | |
| 5,634,928 A | 6/1997 | Fischell et al. | |
| 5,662,675 A | 9/1997 | Polanskyj Stockert et al. | |
| 5,683,451 A | 11/1997 | Lenker et al. | |
| 5,695,499 A * | 12/1997 | Helgerson et al. | 606/108 |
| 5,800,526 A | 9/1998 | Anderson et al. | |
| 5,807,101 A | 9/1998 | Scalzo | |
| 5,817,101 A * | 10/1998 | Fiedler | 623/1.11 |
| 5,843,164 A | 12/1998 | Frantzen et al. | |
| 5,860,998 A | 1/1999 | Robinson et al. | |
| 5,989,280 A * | 11/1999 | Euteneuer et al. | 623/1.1 |
| 6,022,336 A * | 2/2000 | Zadno-Azizi et al. | 604/101.05 |
| 6,042,589 A * | 3/2000 | Marianne | 606/108 |
| 6,056,759 A * | 5/2000 | Fiedler | 623/1.11 |
| 6,068,634 A * | 5/2000 | Lorentzen Cornelius et al. | 623/1.11 |
| 6,102,942 A | 8/2000 | Ahari | |
| 6,168,610 B1 | 1/2001 | Marin et al. | |
| 6,183,443 B1 | 2/2001 | Kratoska et al. | |
| 6,290,710 B1 * | 9/2001 | Cryer et al. | 606/200 |
| 6,322,586 B1 | 11/2001 | Monroe et al. | |
| 6,468,244 B1 | 10/2002 | Leone et al. | |
| 6,544,223 B1 | 4/2003 | Kokish | |
| 6,607,551 B1 * | 8/2003 | Sullivan et al. | 623/1.11 |
| 6,613,075 B1 | 9/2003 | Healy et al. | |
| 2001/0044648 A1 | 11/2001 | Wolinsky et al. | |
| 2003/0050684 A1 * | 3/2003 | Abrams et al. | 623/1.11 |
| 2003/0163155 A1 | 8/2003 | Haverkost et al. | |
| 2004/0133263 A1 | 7/2004 | Dusbabek et al. | |

FOREIGN PATENT DOCUMENTS

| | | |
|---|---|---|
| EP | 0 684 022 | 11/1995 |
| WO | WO 96/24308 | 8/1996 |
| WO | WO-98/09583 A | 3/1998 |
| WO | WO 98/53761 | 12/1998 |
| WO | WO 99/47075 | 9/1999 |
| WO | WO 99/49812 | 10/1999 |
| WO | WO-01/10345 A1 | 2/2001 |

OTHER PUBLICATIONS

U.S. Appl. No. 09/442,165, filed Nov. 16, 1999 to Choulnard et al.
U.S. Appl. No. 09/442,192, filed Nov. 16, 1999 to Zarbatany et al.
U.S. Appl. No. 09/574,418, filed May 19, 2000 to Sullivan et al.
U.S. Appl. No. 09/852,524, filed May 10, 2001 to Elliott.
U.S. Appl. No. 10/080,791, filed Feb. 22, 2002 to Haverkost et al.
U.S. Appl. No. 10/081,636, filed Feb. 22, 2002 to Thompson et al.
English translation of Japanese Office Action for Japanese Application No. 2003-570736 mailed on Jan. 6, 2009.
Canadian Office Action dated May 28, 2009 for related Canadian Patent Application No. 2,476,734. 11 pgs.
International Search Report for Corresponding PCT/US03/04943, Mail date Aug. 5, 2003.
International Search Report for Corresponding PCT/US03/04662, Mail date Jul. 3, 2003.

* cited by examiner

METHOD AND APPARATUS FOR DEPLOYMENT OF AN ENDOLUMINAL DEVICE

TECHNICAL FIELD

This invention relates generally to endoluminal devices and, more specifically, to methods and apparatus for deploying endoluminal devices in body lumens.

BACKGROUND OF THE INVENTION

A stent is an elongated device used to support an intraluminal wall. In the case of a stenosis, a stent provides an unobstructed conduit through a body lumen in the area of the stenosis. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stentgraft. A stent-graft may be used, for example, to treat a vascular aneurysm by removing the pressure on a weakened part of an artery so as to reduce the risk of rupture. Other devices, such as filters, particularly vena cava filters, may have similar structures to stents and may be placed in a body lumen by similar methods. As used herein, the term "endoluminal device" refers to covered and uncovered stents, filters, and any other device that may be placed in a lumen. The term "stent" as used herein is a shorthand reference referring to a covered or uncovered stent.

Typically, an endoluminal device, such as a stent-graft deployed in a blood vessel at the site of a stenosis or aneurysm, is implanted endoluminally, i.e. by so-called "minimally invasive techniques" in which the device, restrained in a radially compressed configuration by a sheath or catheter, is delivered by a delivery system or "introducer" to the site where it is required. The introducer may enter the body from an access location outside the body, such as through the patient's skin, or by a "cut down" technique in which the entry blood vessel is exposed by minor surgical means. The term "proximal" as used herein refers to portions of the stent or delivery system relatively closer to this access location, whereas the term "distal" is used to refer to portions farther from the access location.

When the introducer has been threaded into the body lumen to the stent deployment location, the introducer is manipulated to cause the stent to be ejected from the surrounding sheath or catheter in which it is restrained (or alternatively the surrounding sheath or catheter is retracted from the stent), whereupon the stent expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Figure 1A:
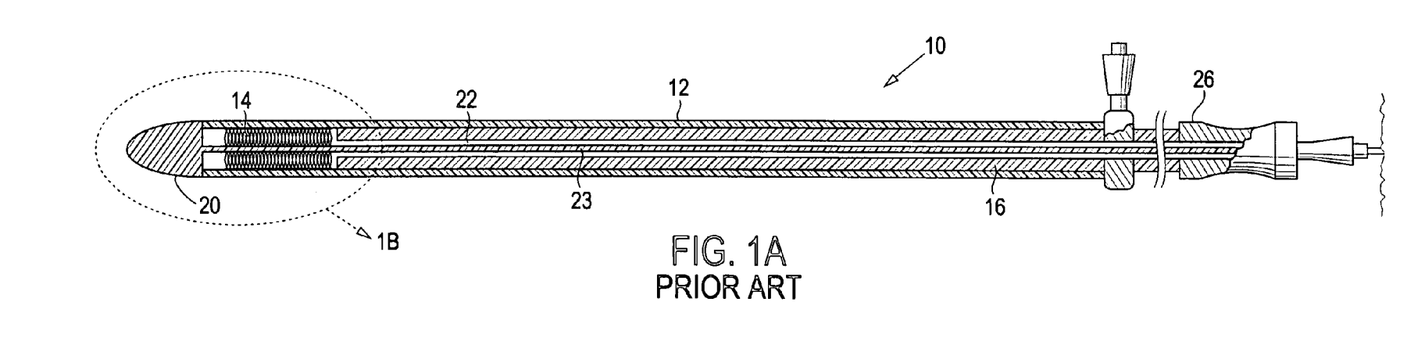
FIG. 1A shows a longitudinal section of a standard introducer of the prior art.
Figure 1B:
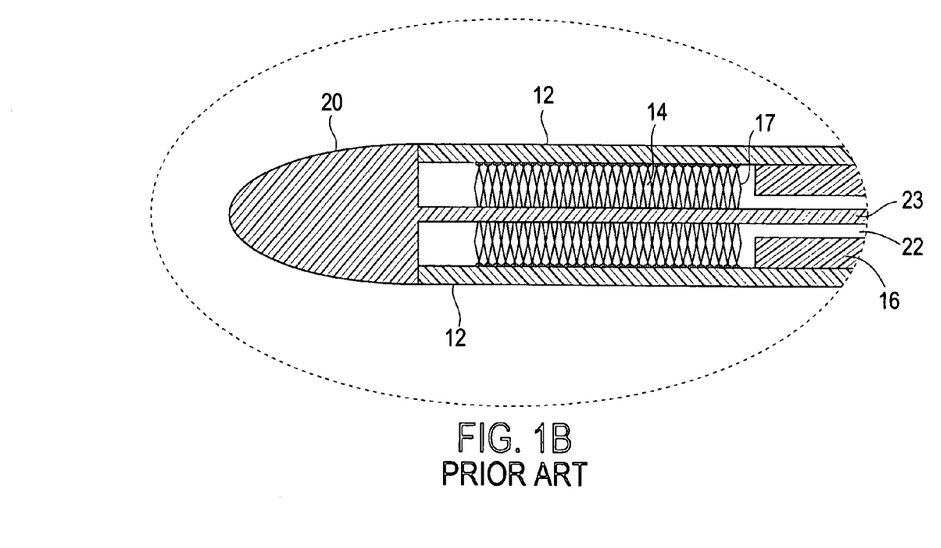
FIG. 1B shows a detailed longitudinal section of the encircled portion of FIG. 1A.

Referring now to a typical prior art introducer as seen in FIGS. 1A and 1B, there is shown a standard pre-loaded delivery system 10 comprising an outer sheath 12, a compressed endoluminal device 14 loaded therein, and a conventional stabilizer 16 loaded adjacent to the proximal end 17 of the endoluminal device. A standard deployment technique comprises maneuvering the introducer to a desired deployment location and retracting outer sheath 12 so that the endoluminal device is deployed beginning at its distal end and ending at its proximal end. Stabilizer 16 stabilizes or prevent retraction of endoluminal device 14 when sheath 12 is retracted, thus effecting deployment of the device into a desired location by forcing relative movement between the sheath and the device.

Delivery system 10 also may comprise a catheter tip 20 at its distal end attached to an internal shaft 23 that runs through the delivery system through inner lumen 22 in stabilizer 16, as shown in FIG. 1A. A stabilizer handle 26 is typically located at the proximal end of stabilizer 16, outside the body lumen. Internal shaft 23 may guide the delivery system through the body lumen over a guidewire (not shown) to the area to be repaired, or may be adapted for inflating a balloon (if applicable), and/or for flushing the system.

It is often important during endoluminal device delivery to ensure accurate placement of the device termini, particularly in intravascular deployment of multipart stents. Improper stent placement can prevent successful medical treatment. There is a particular need in the art to anchor the proximal end of a self-expanding stent while deploying the distal end, and also to provide accurate deployment of self-expanding stents in a way that prevents recoil of the endoluminal device upon release, which may adversely affect the accuracy of the device placement. Balloons are commonly used to anchor endoluminal devices during deployment, but the pressure of a balloon against a vessel wall may damage tissue, particularly if the vessel wall is already diseased. Thus, it is further desirable to anchor the proximal end of an endoluminal device while deploying the distal end without applying unnecessary force against the vessel wall.

In a procedure to repair an abdominal aortic aneurysm (AAA), use of a modular self-expanding stent involves accurate placement of a terminus of a first stent component in the abdominal aorta just below the renal arteries. A second stent component is then deployed in the first stent component and permitted to extend to a terminus in one of the iliac arteries. It is difficult, however, to ensure accurate placement of the iliac terminus of the second stent component. If the terminus is not placed far enough into the iliac, then the stent may be ineffective. If the terminus extends too far, it may interfere with blood flow in arteries branching from the iliac, such as the internal iliac artery. This problem also occurs in the deployment of multipart stents in other branched arteries. Thus, it is desirable to provide a way to ensure accurate deployment of all the termini of a multipart stent.

SUMMARY OF THE INVENTION

In accordance with this invention, there is provided an introducer having a retrograde portion and an anterograde portion for deployment of an endoluminal device in a distal location from a proximal location. The introducer comprises, in a most basic embodiment, a shaft having a distal tip; an inner sheath mounted concentrically over the shaft with the endoluminal device mounted concentrically over the inner sheath; and an anterograde sheath attached proximally to the distal tip, mounted over the endoluminal device in the anterograde portion of the introducer, and axially moveable relative to the inner sheath by moving the shaft. The introducer may further comprise anchoring means in at least one of the retrograde portion or the anterograde portion for anchoring the endoluminal device during deployment of the device from its proximal end to its distal end.

In one embodiment, the anchoring means comprises an inflatable balloon in the retrograde portion. A proximally retractable retrograde sheath may be mounted concentrically over the shaft and inner sheath and may extend axially over the proximal end of the endoluminal device and the balloon. A medial sheath may be mounted concentrically between the inner sheath and the retrograde sheath in the retrograde portion of the introducer proximal the balloon.

In another embodiment, the anchoring means comprises a holder in the anterograde portion. The holder may be concentrically mounted to the inner sheath and adapted to prevent distal movement of the endoluminal device during advancement of the anterograde shaft. The anterograde sheath may extend over an entire length of the endoluminal device.

In another embodiment, the introducer comprises the proximally retractable retrograde sheath and the medial sheath, wherein the anchoring means comprises an extended portion of a proximal end of the endoluminal device and a notch in one or both of the medial sheath and the retrograde sheath for releasably confining the extended portion between the retrograde sheath and the medial sheath with the retrograde sheath in a first position and for releasing the extended portion with the retrograde sheath in a second, retracted position relative to the medial sheath.

In yet another embodiment, the anchoring means comprises a tether attached to a proximal end of the endoluminal device. In an embodiment comprising the proximally retractable retrograde sheath and the medial sheath, the tether may be attached to one of the medial sheath, the retrograde sheath, or the inner sheath. In another embodiment, the tether may extend proximally from the device a sufficient distance to terminate outside a body lumen through which the introducer is adapted to be introduced. In such an embodiment, the medial sheath may comprise a lateral channel through which the tether extends.

Still another embodiment of the present invention comprises an introducer having a retrograde portion and an anterograde portion and comprising an inflatable balloon mounted radially inside the retrograde portion for anchoring the endoluminal device during deployment of the device from its proximal end to its distal end. The anterograde portion comprises a distal tip and an anterograde sheath attached proximally to the distal tip. A shaft attached to the distal tip and extending concentrically through a central lumen defined by the anterograde portion and retrograde portion is adapted for moving the anterograde portion relative to the retrograde portion. The endoluminal device is mounted concentrically over the shaft in the central lumen and has a distal end contained by the anterograde portion and a proximal end contained by the retrograde portion. The introducer may further comprise an inner sheath mounted concentrically over the shaft underneath the endoluminal device, the inner sheath defining a lumen connected to an inner region of the inflatable balloon for communication of a fluid to the balloon for inflation of the balloon. The retrograde portion comprises a proximally retractable retrograde sheath mounted concentrically over the shaft and inner sheath and extending distally over the balloon and a retrograde portion of the endoluminal device.

The invention also comprises a method for deployment of an endoluminal device in a distal location in a body lumen from a proximal location. The method comprises the steps of inserting an introducer of the present invention into a body lumen, aligning the introducer in a deployment location, extending the shaft to distally advance the anterograde sheath to deploy at least the anterograde portion of the endoluminal device, and then removing the introducer from the body lumen. Where the introducer comprises anchoring means in the anterograde portion, the method comprises aligning the proximal end of the device with the deployment location, and confining the endoluminal device between the anchoring means and the advancing anterograde sheath during advancement of the anterograde sheath. Where the anchoring means are in the retrograde portion, the method comprises anchoring the proximal end during advancement of the anterograde sheath and releasing the proximal end prior to or concurrently with removal of the introducer from the lumen.

Where the anchoring means comprises an inflatable balloon, the method comprises inflating the balloon prior to deployment of the anterograde portion of the endoluminal device and deflating the balloon after deployment of the anterograde portion. Where a retrograde sheath is present, the retrograde sheath may be retracted prior to inflating the balloon, such that the balloon is inflated to anchor the proximal end of the endoluminal device against the body lumen. In the alternative, the balloon may be inflated to anchor the proximal end of the endoluminal device against the retrograde sheath, in which case the retrograde sheath is not retracted until after deflating the balloon after the anterograde portion of the endoluminal device has been deployed.

Where the anchoring means comprises a tether, the method comprises separating the tether from the endoluminal device prior to or during removal of the introducer from the body. Where the anchoring means comprises an extended portion of the endoluminal device releasably confined in a notch between the retrograde sheath and the medial sheath or between the retrograde sheath and the inner sheath, the method comprises retracting the retrograde sheath sufficient to release the extended portion from the notch after deployment of the anterograde portion of the endoluminal device.

For the embodiment wherein the retrograde portion comprises an inflatable balloon mounted inside the retrograde portion, an exemplary method comprises aligning the introducer in a deployment location, retracting at least part of the retrograde portion and deploying the proximal end of the endoluminal device. The balloon is then inflated to compress the endoluminal device against the lumen wall while the shaft is extended to distally advance the anterograde sheath to deploy a remaining portion of the endoluminal device.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 2:
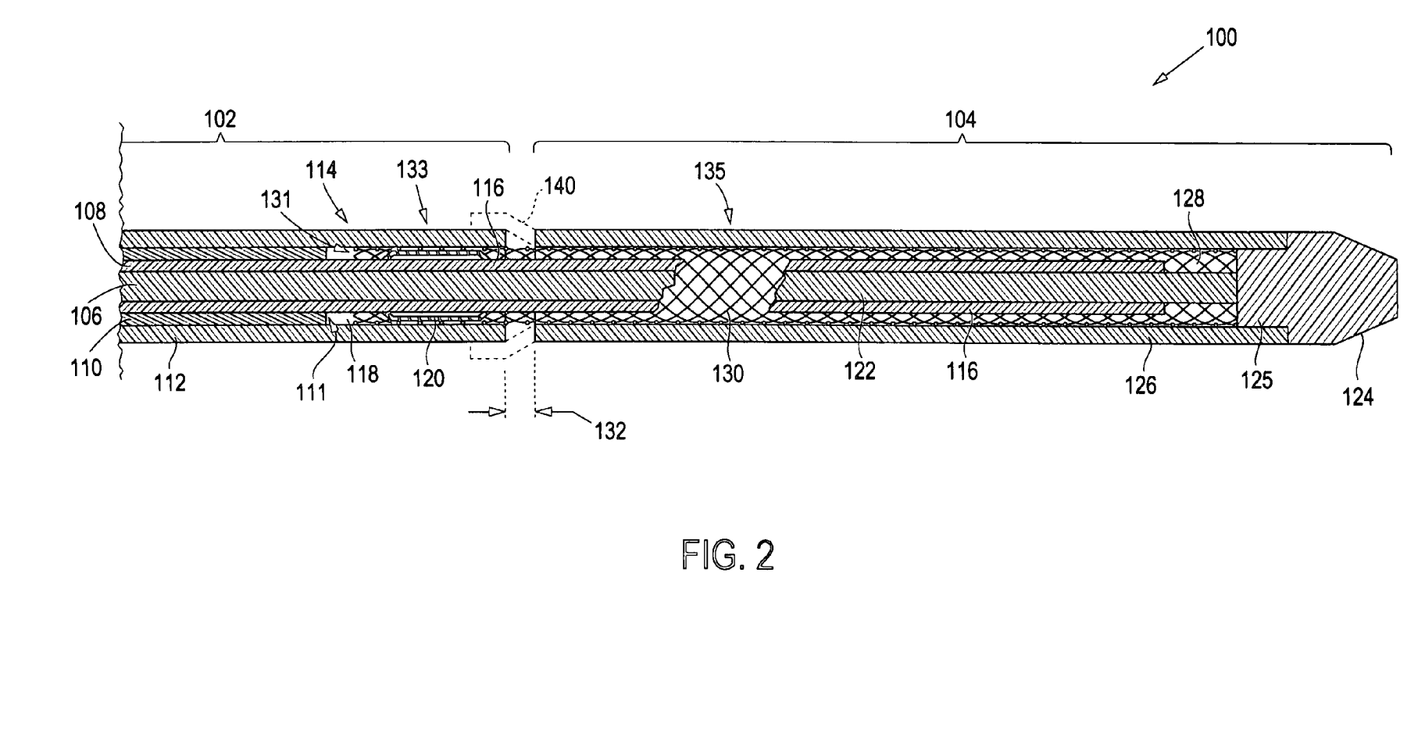
FIG. 2 shows a longitudinal section of an exemplary introducer of the present invention.

Referring now to FIG. 2 there is shown an exemplary introducer embodiment of the present invention. Introducer 100 comprises a retrograde portion 102 and an anterograde portion 104. Shaft 106 may be solid or tubular, and is surrounded by three concentrically positioned sheaths: inner sheath 108, medial sheath 110, and retrograde sheath 112. Medial sheath 110 preferably has a fixed position and operates as a radial spacer, separating retrograde sheath distal extension 114 from inner sheath distal extension 116. The distal extension 114 of retrograde sheath 112 and distal extension 116 of inner sheath 108 comprise the respective portions of those sheaths located distally of the distal end 111 of medial sheath 110.

Other types of spacers may also be used. For example, radial protrusions on inner sheath or retrograde sheath may provide such spacing. Furthermore, inner sheath may have a stepped outside diameter or retrograde sheath may have a stepped inside diameter, such as created by medial sheath being fused to either inner sheath or retrograde sheath, or by any other method that creates an equivalent structure.

Radial space 118 between retrograde sheath 112 and inner sheath 108 may be sufficiently large to allow room for a radial-force-exerting device, such as balloon 120. Inner sheath 108 preferably has a fixed position and may include a lumen for communicating pressurized fluid to balloon 120. Although shown in FIG. 2 with balloon 120 and proximal end 131 of device 130 as part of retrograde portion 102 covered by retrograde sheath 112, in an alternative embodiment shown in FIG. 7, balloon 120 and proximal end 131 of device 130 may be part of anterograde portion 104 and covered by anterograde sheath 126.

Anterograde portion 104 of introducer 100 includes a distal extension 122 of shaft 106 and distal extension 116 of inner sheath 108. Distal extension 122 of shaft 106 terminates with an attachment to radial spacer 125 connected to distal tip 124. Distal tip 124 is coupled to anterograde sheath 126, which extends proximally from distal tip 124, and is positioned concentrically about shaft distal extension 122 and inner sheath distal extension 116. Radial spacer 125 creates an area 128 into which an endoluminal device 130, such as a stent graft, can be loaded.

Retrograde sheath 112 and anterograde sheath 126 may have a lateral space 132 therebetween, the sheaths may abut one another (not shown) without any space 132, or the sheaths may laterally overlap one another as depicted by dashed lines 140 in FIG. 2. Dashed lines 140 show a proximal extension of anterograde sheath 126 that overlaps retrograde sheath 112.

In an alternative embodiment, a similar distal extension (not shown) of retrograde sheath 112 may laterally overlap anterograde sheath 126.

Figure 3:
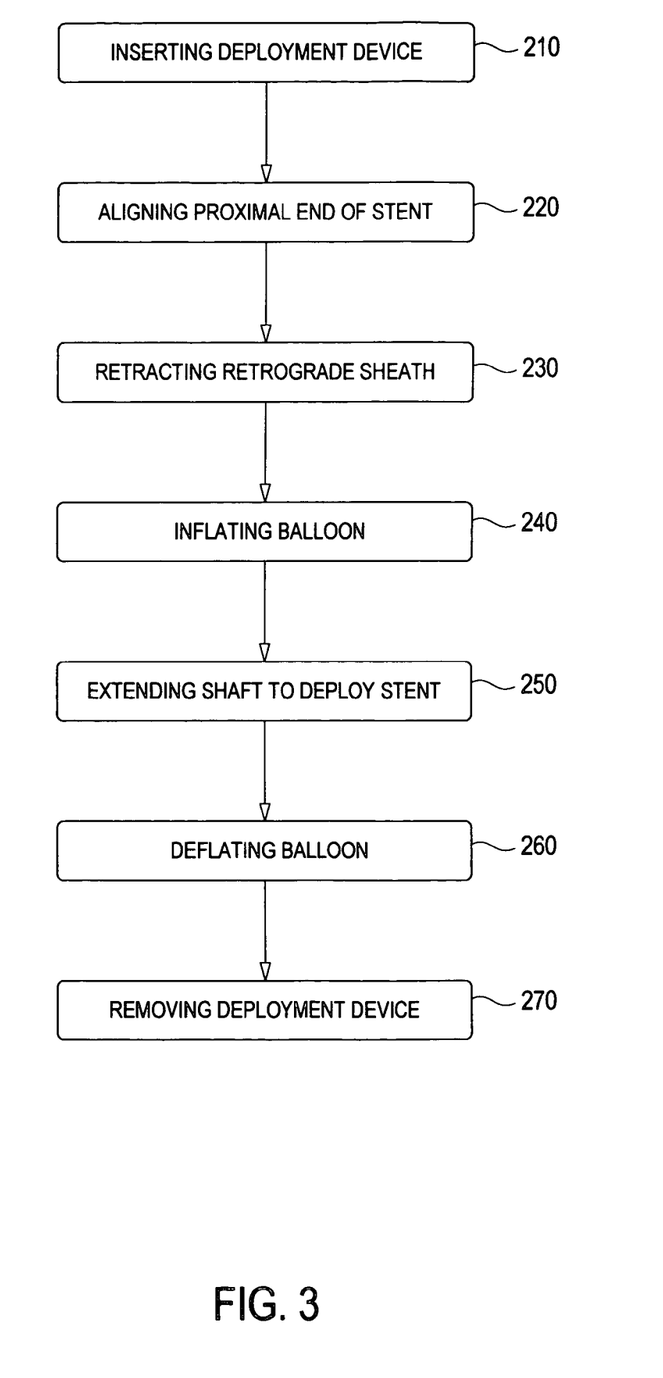
FIG. 3 shows a flowchart depicting an exemplary method of the invention.

An exemplary method for using introducer 100 is depicted in the flowchart shown in FIG. 3. The method may be performed, for example, in an operating room or an angiographic suite, preferably under fluoroscopic guidance as is known in the art. First, the introducer is inserted into a body lumen, as indicated in step 210, distal tip 124 first, from a proximal access site, such as a femoral artery or iliac artery, for vascular deployment. Typically, the introducer is threaded into the lumen over a guidewire (not shown) as is well known in the art. The access site may be surgically exposed and punctured with, for example, an 18-gauge needle as is known in the art.

Next, in step 220, the proximal end 131 of endoluminal device 130 is aligned in an appropriate deployment position. Fluoroscopic guidance and/or a guide wire may be used to guide proximal end 131 into the desired position. For example, where endoluminal device 130 is an AAA stent graft, proximal end 131 of device 130 is positioned in the iliac (not shown), preferably just above a branch of the internal iliac artery (not shown).

Figure 7:
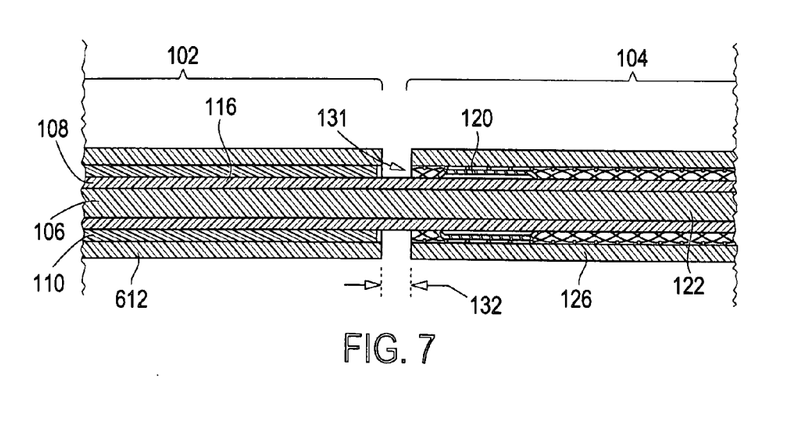
FIG. 7 shows a portion of a longitudinal section of another exemplary introducer of the present invention in which the balloon is contained within the retrograde portion.

Then, in step 230, retrograde sheath 112 is retracted at least far enough to expose proximal end 131 of device 130 and balloon 120. In an alternative embodiment wherein the proximal end 131 and balloon 120 are located under anterograde sheath 126, the anterograde sheath 126 is initially advanced far enough to expose the proximal end and balloon. Balloon 120 is inflated in step 240, such as by pressurizing balloon 120 with fluid communicated via a lumen in inner sheath 108, to exert radial force that compresses the retrograde portion 133 of device 130 against the lumen wall (not shown). Although the various lumens are shown concentrically, other configurations, including side-by-side lumen can be used. Such other configurations are described in an application titled "APPARATUS AND METHOD FOR DEPLOYMENT OF AN ENDOLUMINAL DEVICE," by Johnson et al., Ratner & Prestia docket number BSI-498US, filed the same day as this application and assigned to the common assignee of this application, incorporated herein by reference. In step 250, shaft 106 is extended distally to deploy the anterograde portion 135 of device 130. Prior to extending the shaft, the guidewire and retrograde sheath 112 may typically be locked together to prevent movement of the retrograde sheath or the guidewire during extension of the shaft. As used herein, the "retrograde portion" of device 130 refers to any portion initially covered by the retrograde sheath (as shown in FIG. 2) or any portion underlied by balloon 120 and any portion proximal thereof (as shown in FIG. 7), and the "anterograde portion" refers to the remainder of the device distal of the retrograde portion. Balloon 120 is then deflated in step 260 and introducer 100 is removed from the lumen in accordance with step 270. If desired, prior to removal from the lumen, balloon 120 may be used for modeling device 130 to better conform to the contours of the lumen wall, as is known in the art. Thus, introducer 100 and the method depicted in FIG. 3 provides means for accurately placing the proximal end of an endoluminal device.

In an alternative method, step 240 of inflating balloon 120 may be carried out prior to step 230 of retracting retrograde sheath 112, so that the balloon exerts radial force compressing retrograde portion 133 of device 130 into the retrograde sheath. Then, after step 250 of extending shaft 106 to deploy anterograde portion 135 of device 130, balloon 120 is deflated in step 260 and retrograde sheath 106 is retracted in step 230 to complete deployment of the retrograde portion of the device. Finally, the introducer is removed in step 270. Thus, in a first method, the steps are performed in numerical order as shown in FIG. 3, and in a second method, the steps are performed in the step order 210-220-240-250-260-230-270. The second method has the advantage that the balloon does not press against the lumen wall, but instead presses against the retrograde sheath, thus avoiding exertion of stress on the lumen wall. This second method is particularly desirable in the case of diseased lumen walls, which could be damaged due to the force of the balloon. This method, however, may sacrifice a few millimeters of accuracy due to recoil of the device 130. Consequently, the second method may be more desirable for applications in which the small sacrifice in accuracy is medically acceptable.

Figure 4A:
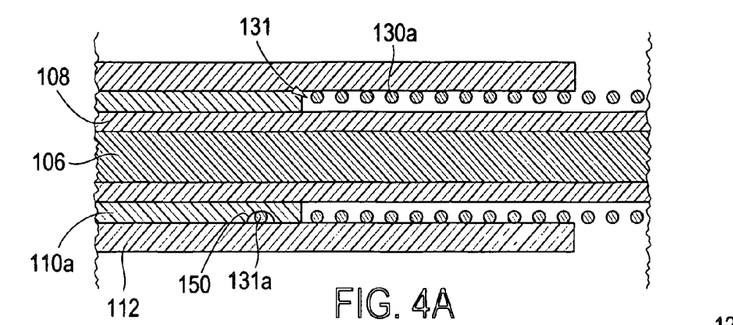
FIG. 4A shows a longitudinal section of a portion of an exemplary introducer of the present invention having an extended cell and notch anchoring arrangement and a medial sheath.

As an alternative to balloon 120, other means for holding proximal end 131 of device 130 may be employed. For example, as shown in FIG. 4A, a notch 150 may be located in medial sheath 110a. A proximally extended portion 131a of device 130a, such as an extended cell or a loop, is fixed within notch 150. In the method shown in FIG. 3, the retrograde sheath 112 is only retracted in step 230 until the proximal end 131 of stent 130 deploys, except for proximally extended portion 131a. A radiopaque deployment marker (not shown) may be used to mark the end 131 so that the retrograde sheath is not retracted too far. Steps 240 and 260 are omitted from the method steps, as proximally extended portion 131a remains compressed in notch 150 between medial sheath 110a and retrograde sheath 112 to hold the proximal end 131 of device 130 in place until the distal portion of the stent has been deployed. Then, prior to removing deployment device in step 270, retrograde sheath 112 is retracted the remaining distance necessary to release proximally extended portion 131a from notch 150.

Figure 5A:
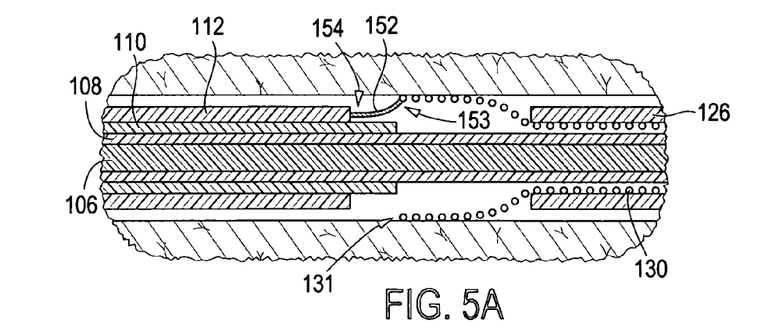
FIG. 5A shows a longitudinal section of a portion of an exemplary introducer of the present invention having a tether attached to the retrograde sheath for anchoring the proximal end of the endoluminal device.

In yet another alternate embodiment, shown in FIG. 5A, a tether 152 may be used for anchoring. Distal end 153 of tether 152 is attached to proximal end 131 of device 130 and proximal end 154 of the tether may be attached to the distal end of either retrograde sheath 112 (as shown in FIG. 5A) or medial sheath 110 (not shown), or to an intermediate portion of inner sheath 108 (shown in FIG. 5C). Tether 152 may be attached to device 130 and sheath 112 or 110 in any way known in the art, such as by gluing, suturing, stapling, welding, heat shrinking, and the like. The tether may comprise any type of material known in the art, including metal or non-metal filaments. Preferably, the tether is attached to the device in such a way that it is readily detachable from the device when desired. Suitable mechanisms for detachably connecting a wire to an implantable device are described in U.S. Pat. Nos. 5,354,295 and 5,122,136 to Guglielmi et al., as well as in U.S. patent application Ser. No. 09/852,524, filed on May 10, 2001, by Chris Elliott on behalf of the assignee of this invention, all of which are incorporated herein by reference.

Figure 5B:
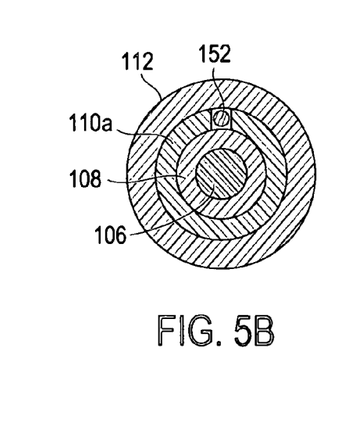
FIG. 5B shows a cross section of a portion of another embodiment of an exemplary introducer of the present invention having a channel in the medial sheath for the tether.

Although shown in FIG. 5A attached to the distal end of retrograde sheath 112, tether 152 may be employed in any way known in the art, including extending proximally all the way back to the access location outside the body lumen. For example, as shown in the cross-sectional illustration of FIG. 5B, medial sheath 110a may have a lateral channel running its entire length into which tether 152 may extend. Thus, tether 152 may connect to a power supply or a handle for exerting tensional or torsional force, as described in the '524 application.

For tethered embodiments, the method is carried out as shown in FIG. 3 up to step 230, at which point the retrograde sheath 112 is retracted until proximal end 131 of the device 130 deploys, with tether 152 holding proximal end 131 in place. The guidewire is then typically locked with retrograde sheath 112 to prevent further movement of the retrograde sheath 112, and anterograde sheath 126 is advanced by advancing shaft 106 to deploy the anterograde portion of device 130. Then, the remainder of retrograde sheath 112 is retracted as part of step 270 to release device 130 from tether 152. If proximal end 154 of tether 152 is attached to medial sheath 110 instead of retrograde sheath 112, the medial sheath may be retracted, or if the medial sheath is not retractable, the entire introducer may be retracted to release device 130 from tether 152 in step 270.

Figure 6:
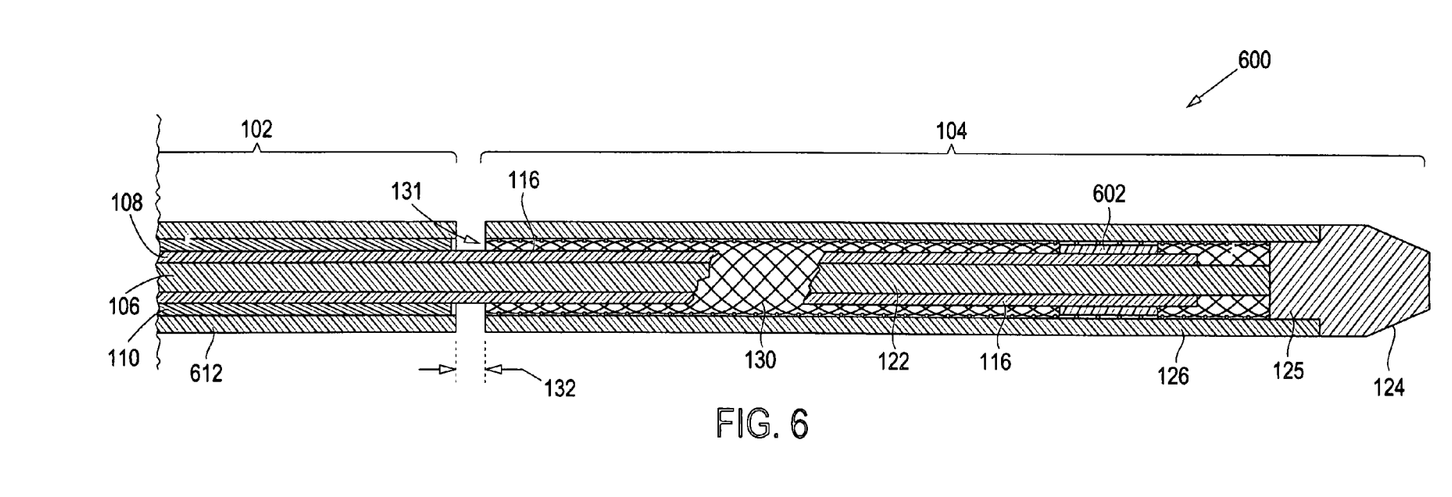
FIG. 6 shows a longitudinal section of another exemplary introducer of the present invention having a holder at the distal end of the endoluminal device.

Another introducer embodiment 600 is shown in FIG. 6. In this embodiment, all of the components are essentially the same as in embodiment 100, except that instead of a combination of balloon 120 and retrograde sheath 112 at the proximal end, there is a holder 602 near the distal end of inner sheath extension 116. Anterograde sheath 126 (and thus anterograde portion 104 of introducer 600) extends to the proximal end 131 of device 130. Holder 602 may comprise any material known in the art and may have any geometry known in the art sufficient to hold device 130 in place while anterograde sheath is advanced. A number of geometries and materials useful for holding a stent in place from inside the stent are described in U.S. application Ser. No. 09/574,418 by Sullivan et al., filed on May 19, 2000, assigned to the assignee of this invention, and incorporated herein by reference. For example, holder 602 may be a sleeve of a relatively higher friction material than sheath 126 such that device 130 is frictionally retained while sheath 126 advances. In another embodiment, holder 602 may comprise one or more radial protrusions that exerts an axial restraining force against individual members of device 130. Other structures or combinations of multiple structures may also be used as holders.

A holder 602 at or near the distal end of device 130 as shown in FIG. 6 may be beneficial for combination with a balloon at or near the proximal end of the device as shown in FIG. 7. Such a holder 602 may minimize potential distal advancement of proximal end 131 of device 130 during the initial advancement of sheath 126 to expose balloon 120, as may otherwise potentially occur as a result of frictional contact between the anterograde sheath and the device. In the embodiment shown in FIG. 7, balloon 120 may also be provided with a greater frictional engagement force than sheath 126 so that device 130 tends to stay with the balloon rather than move with the sheath. Such a greater frictional engagement force may be the result of a higher coefficient of friction, for example.

Thus, the method of using introducer 600, referring back to FIG. 3, involves steps 210, 220, 250, and 270, without any of the steps relating to the balloon or the retrograde shaft. In fact, the embodiment shown in FIG. 6 may comprise a minimal set of components comprising shaft 106, inner sheath 108, holder 602 mounted directly to the inner sheath 108, and tip 124 attached to anterograde sheath 126. The remaining components shown in FIG. 6 are optional.

Holder 602 is not limited to restraining only the distal end of device 130. For example, holder 602 may extend the length of device 130, an embodiment that may be particularly useful with devices having a relatively low column strength. A hybrid of introducers 100 and 600 may also be provided comprising both a holder 602 and a balloon 120 or other anchoring means at proximal end 131 of device 130, with anterograde sheath 126 extending over the proximal end of the device. In such a configuration comprising a balloon, the deployment method follows the method steps in the order shown in FIG. 3, except that in step 230 instead of retracting retrograde sheath 112, the method comprises advancing anterograde sheath a sufficient distance to uncover balloon 120, and then inflating the balloon at step 240 and continuing on with the remainder of the method steps. As balloon 120, once inflated, is capable of anchoring device 130, holder 602 may be located closer to proximal end 131 of the device so that it engages the device only during the initial advancement of anterograde sheath 126 prior to inflation of the balloon.

Figure 4B:
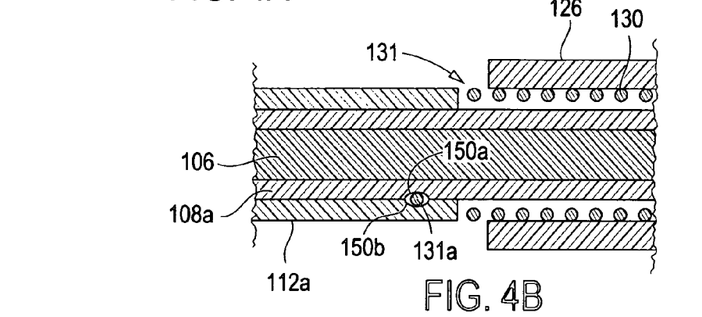
FIG. 4B shows a longitudinal section of a portion of another exemplary introducer of the present invention having an extended cell and notch anchoring arrangement with no medial sheath.

Tethered or extended-portion-and-notch embodiments may also be provided with anterograde sheath 126 extending to the proximal end of endoluminal device 130. In an extended-portion-and-notch embodiment shown in FIG. 4B, there may be no medial sheath, such that retrograde sheath 112a directly contacts inner sheath 108a, and the notch 150 may be in inner sheath 108a, retrograde sheath 112a, or may comprise notch portions 150a and 150b in each, respectively, as shown in FIG. 4B. The medial sheath may optionally be present, such as to preserve a constant radial profile throughout the introducer, in which case the notch or a portion of the notch may be located in one or both of the retrograde sheath and the medial sheath. The method of using such an embodiment comprises inserting the device in step 210, aligning the proximal end in step 220, extending the shaft to deploy the device 250, and then retracting the retrograde sheath in step 230 a sufficient distance to release the extended portion from the notch.

Figure 5C:
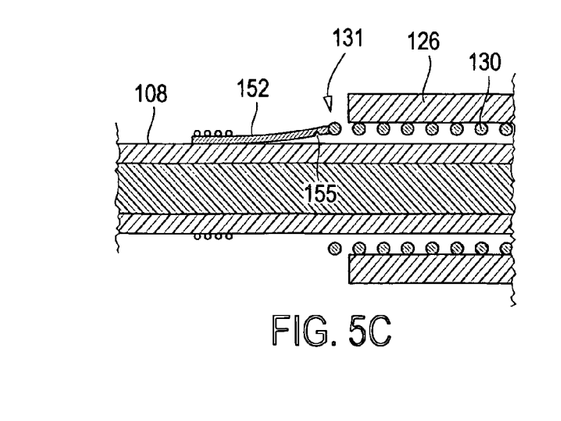
FIG. 5C shows a longitudinal section of a portion of another exemplary introducer embodiment of the present invention having a tether attached to the inner sheath for anchoring the proximal end of the endoluminal device.

In a tethered embodiment with anterograde sheath 126 extending to the proximal end of endoluminal device 130, as shown in FIG. 5C there may be no medial sheath or retrograde sheath, and tether 152 may just be attached to an intermediate portion of inner sheath 108 as shown in FIG. 5C, or may extend freely (not shown) through the lumen back through the access location and outside the lumen to some means for manipulating the tether, such as the means shown and described in '524 application. As shown in FIG. 5C, tether 152 is wrapped about inner sheath 108 in a manner than fixes it axially and may be further anchored in place with an adhesive. Notch 155 in tether provides a predetermined weak spot so that the retraction of the introducer is sufficient to break the tether at the notch. It is important that the amount of force required to break tether 152 at a preferred location, such as notch 155, is less than the amount of force that will break the tether in other locations or remove the affixation of the tether to inner sheath, more than the amount of force necessary to hold proximal end 131 of endoluminal device 130 in place during deployment of its distal end (so that it does not break prematurely), and less than the amount of force that will axially move device 130 once deployed in the lumen (so that breaking the tether does not take the deployed device out of its proper alignment). The tether may also be affixed in a slipknot that requires an amount of force to undo the knot that does not break the tether, pull the deployed device out of alignment, or undo prematurely.

One concern of the reverse deployment method and introducers described herein is that if the anterograde portion is too long, it may enter the heart during deployment of an AAA stent graft. Other, non-AAA applications may have similar concerns with surrounding organs or other body structure. Thus, the dimensions of the introducer may be optimized to prevent damage caused by the anterograde portion being too long. One way of shortening the anterograde portion for a particular application is to lengthen the retrograde portion. Thus, although shown in FIGS. 2 and 6 with anterograde portion extending over the majority of the length of device 130, in other embodiments the anterograde portion and retrograde portions may extend over equal lengths of the device, or portion of the device over which the retrograde portion extends may be longer than the portion over which the anterograde portion extends. Such embodiments, for example an introducer wherein the retrograde and anterograde portions extend over equal lengths of the device, may be useful where the location of the proximal end of the device is less important than aligning the middle of the device with a certain region of a lumen.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An introducer, having a retrograde portion and an anterograde portion, for deployment of an endoluminal device in a body lumen in a distal location from a proximal location, the device having a compressed configuration and an expanded configuration, the introducer comprising:
    a shaft having a distal tip;
    an inner sheath mounted concentrically over the shaft, wherein the endoluminal device is mounted concentrically over the inner sheath in the compressed configuration;
    an anterograde sheath attached proximally to the distal tip, mounted over at least a distal portion of the endoluminal device in the anterograde portion of the introducer, the anterograde sheath having an open proximal end such that distal movement of the anterograde sheath unsheathes the portion of the endoluminal device contained thereunder;
    anchoring means, comprising an inflatable balloon, in only the retrograde portion configured to:
        engage an anchor only a proximal portion of the endoluminal device against the body lumen during the unsheathing of a distal portion of the endoluminal device; and
        minimize relative axial movement between the engaged and anchored proximal portion of the device and the body lumen during unsheathing of the distal portion of the endoluminal device; and
    a proximally retractable retrograde sheath mounted concentrically over the shaft and inner sheath in the retrograde portion of the introducer and extending distally over a retrograde portion of the endoluminal device, wherein the retrograde sheath and the anterograde sheath are laterally spaced from one another at least when the retrograde sheath is proximally retracted.

2. The introducer of claim 1, wherein the inflatable balloon is at or near a proximal end of the device.

3. The introducer of claim 2, wherein the inner sheath defines a lumen connected to an inner region of the inflatable balloon for communication of a fluid to the balloon for inflation of the balloon.

4. The introducer of claim 2, wherein the inflatable balloon is mounted concentrically underneath a retrograde portion of the endoluminal device.

5. The introducer of claim 4, wherein the proximally retractable retrograde sheath extends distally over the balloon.

6. The introducer of claim 5 further comprising a medial sheath mounted concentrically between the inner sheath and the retrograde sheath in the retrograde portion of the introducer.

7. The introducer of claim 6, wherein the medial sheath has a distal end that terminates proximal of the balloon.

8. The introducer of claim 1 further comprising a radial spacer for providing sufficient space between the inner sheath and the anterograde sheath to contain the endoluminal device.

9. The introducer of claim 8, wherein the radial spacer is attached proximally to the distal tip.

10. The introducer of claim 1 further comprising:
a medial sheath mounted concentrically between the inner sheath and the retrograde sheath in the retrograde portion of the introducer and terminating proximally of a proximal end of the endoluminal device.

11. The introducer of claim 1, wherein the anterograde portion extends over a greater length of the endoluminal device than the retrograde portion.

12. The introducer of claim 1, wherein the retrograde sheath and the anterograde sheath are laterally spaced from one another before the retrograde sheath is proximally retracted.

13. The introducer of claim 1, wherein the retrograde sheath and the anterograde sheath laterally overlap one another before the retrograde sheath is proximally retracted.

14. An introducer for deployment of an endoluminal device in a body lumen in a distal location from a proximal location, the device having a compressed configuration and an expanded configuration, the introducer comprising:
an anterograde portion comprising a distal tip and an anterograde sheath attached proximally to the distal tip and mounted over at least a distal portion of the endoluminal device in the anterograde portion of the introducer, the anterograde sheath having an open proximal end such that distal movement of the anterograde sheath unsheathes the portion of the endoluminal device contained thereunder;
a shaft attached to the distal tip and extending concentrically through a central lumen defined by the anterograde portion and retrograde portion;
an inner sheath mounted concentrically over the shaft;
a retrograde portion including a proximally retractable retrograde sheath mounted concentrically over the shaft and inner sheath in the retrograde portion of the introducer and extending distally over a retrograde portion of the endoluminal device, wherein the retrograde sheath and the anterograde sheath are laterally spaced from one another at least when the retrograde sheath is proximally retracted;
an endoluminal device mounted concentrically over the inner sheath in the central lumen and having a distal portion contained by the anterograde portion and a proximal end contained by the retrograde portion, the distal portion constrained in the compressed configuration by the anterograde sheath and adapted to expand into an expanded state as the anterograde sheath is advanced distally; and
an inflatable balloon mounted radially inside only the retrograde portion and sized to:
engage and anchor the endoluminal device proximal end against the body lumen after expansion of the proximal end into the expanded configuration to minimize relative axial movement between the engaged, anchored, expanded proximal end of the device and the body lumen during unsheathing of the endoluminal device distal portion.

15. The introducer of claim 1, wherein the retrograde sheath and the anterograde sheath abut one another before the retrograde sheath is proximally retracted.

* * * * *